United States Patent [19]

Reeve

[11] 4,268,250

[45] May 19, 1981

[54] ORTHODONTIC APPLIANCE

[76] Inventor: James J. Reeve, 545 Pharr Rd., NE., Atlanta, Ga. 30305

[21] Appl. No.: 54,253

[22] Filed: Jul. 2, 1979

Related U.S. Application Data

[63] Continuation of Ser. No. 797,985, May 18, 1977, abandoned.

[51] Int. Cl.³ .............................................. A61C 7/00
[52] U.S. Cl. .................................................... 433/20
[58] Field of Search ......................................... 433/20

[56] References Cited

U.S. PATENT DOCUMENTS 1,467,789  9/1923  Griffin .................................. 433/20
2,566,414  9/1951  Henry .................................. 433/20
3,762,050  10/1973  Dal Pont .............................. 433/20

OTHER PUBLICATIONS

"The Combination Technique", American Journal of Orthodontics, vol. 49, No. 11, Nov. 1963, pp. 801–814.
"A Survey of Begg Treatment", American Journal of Orthodontics, vol. 49, No. 7, Jul. 1963, pp. 494–506.

*Primary Examiner*—Gene Mancene
*Assistant Examiner*—John J. Wilson
*Attorney, Agent, or Firm*—Newton, Hopkins & Ormsby

[57] ABSTRACT

An orthodontic arch wire is curved in two substantially perpendicular planes, one plane of curvature corresponding to the plane of the normal dental arch, the other plane perpendicular to this. By means of the compound curve arch wire, gentle and consistent pressure can be applied to all teeth in the dental arch simultaneously. These forces are applied through comparatively long lever arms in the appliance. Treatment time is significantly reduced and better cellular response is promoted. The arch wire is pre-looped for space closing and to facilitate attaching elastics.

13 Claims, 7 Drawing Figures

ORTHODONTIC APPLIANCE

This is a continuation of applcation Ser. No. 797,985, filed May 18, 1977, now abandoned.

BACKGROUND OF THE INVENTION

Advances in orthodontics as in general dentistry, have led to a realization in recent times that effective treatment need not be segmented in the mouth of the patient. General dentists have progressed from the stage of filling only one tooth per patient appointment through mouth quadrant dentistry to full mouth reconstruction in appropriate cases. Similarly, in orthodontics, it has been discovered that effective treatment, in fact, greatly improved treatment results are obtainable through application of the appropriate forces to teeth of the entire dental arch simultaneously, rather than selective and progressive application of forces as has been the past practice. It has also been discovered that with proper patient cooperation the traditional rest periods between applications of pressure to the teeth can be dispensed with. If there is no physiological barrier to consistent pressure being used, it should be used to the fullest in order to accomplish the best results in optimum time. Also, the use of consistent pressure without periods of interruption and the application of pressure to the teeth of the full dental arch has recently been found to induce better cellular response and hence a more effective movement of the teeth.

In light of the above knowledge, the present invention has been devised to improve the application of consistent pressure to the teeth in the full dental arch to accelerate orthodontic treatment of patients and to increase the effectiveness of the treatment. In furtherance of these objectives, a compound curve orthodontic arch wire is provided by the invention which can progressively distribute forces to the teeth in the dental arch from the molars in the posterior to the incisors in the anterior. By means of the invention, each tooth can have an equal pressure applied to it as contrasted to straight wire arches with a large tip-back, where comparatively great pressure may be applied to molars and substantially no pressure applied to the anterior teeth.

By means of the invention, consistent pressure is applied simultaneously to all of the teeth in the dental arch, as where the anterior teeth require intrusion. The functioning of the compound curve arch wire embodying the present invention takes advantage of simple mechanics by utilizing moderate forces applied through comparatively long lever arms. It is important that the teeth under pressure have freedom to move with minimum friction in the orthodontic appliance, and one of the prime freatures of the invention is to reduce friction to the absolute minimum obtainable as a practical matter. A further ability of the invention is that the gentle pressure applied to the teeth at the start is not reduced abruptly as the necessary movement of teeth takes place. The gentle pressure consistently applied at the start and throughout the movement process enables cellular action to occur within the periodontial membrane, where the blood supply is adequate to carry away the product of osteoclasts.

The orthodontic arch wire according to the invention is pre-looped, as with a pair of spaced loops, for space closure or maintaining spaces closed during treatment. Thus, it can be seen that a very simple, unitary pre-formed wire appliance can function simultaneously in several different ways to enhance and accelerate orthodontic treatment for the benefit of both patient and orthodontist, economically and in terms of convenience. The many advantages of the invention over prior art practice should be apparent to those skilled in the art.

Some examples of the known patented prior art are contained in U.S. Pat. Nos. 1,638,006; 2,556,414, 2,582,230 and 3,994,068.

DETAILED DESCRIPTION

Figure 3A:
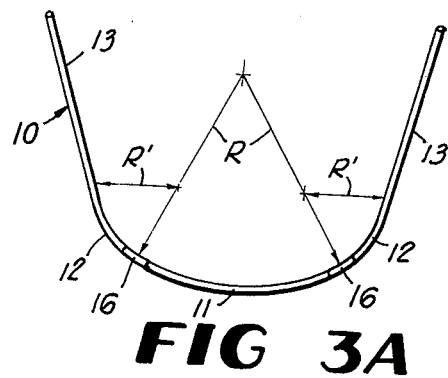
FIG. 3A is a plan view of the arch wire.

Referring to the drawings in detail wherein like numerals designate like parts, a stainless steel arch wire 10 forming the subject matter of this invention is contructed from a single section of wire suitably pre-formed to provide the desired compound curvature and integrated loops. More particularly, referring to FIGS. 2 and 3A, the arch wire 10 is curved in two planes, namely, in the plane of the natural dental arch, FIG. 3A, and normal to the plane of the dental arch, FIG. 2.

As shown in FIG. 3A, the closed anterior portion of the arch wire has a central circularly curved portion 11 formed on a certain radius R and adjacent circularly curved side portions 12 of equal lengths formed on second radii R'. Posteriorly of the curved portions 12, the arch wire has slightly curved divergent arms 13 of the required length and posterior end separation to meet the needs of a particular application. Naturally the dimensions of the radii R and R' and the lengths and posterior end spacing of the arms 13 will vary from case-to-case. However, the plan view configuration of the arch wire 10 in FIG. 3A is substantially that of the natural dental arch.

Figure 2:
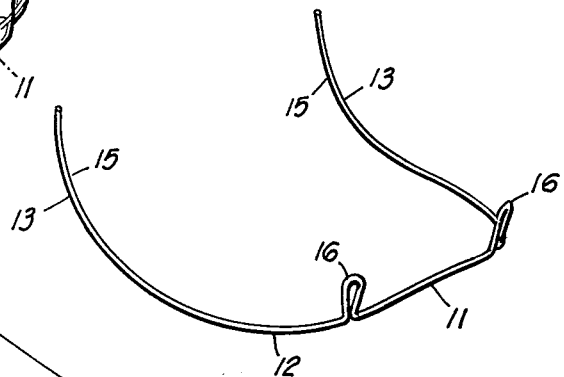
FIG. 2 is an exploded and partly diagrammatic side elevation of the invention.
Figure 2:
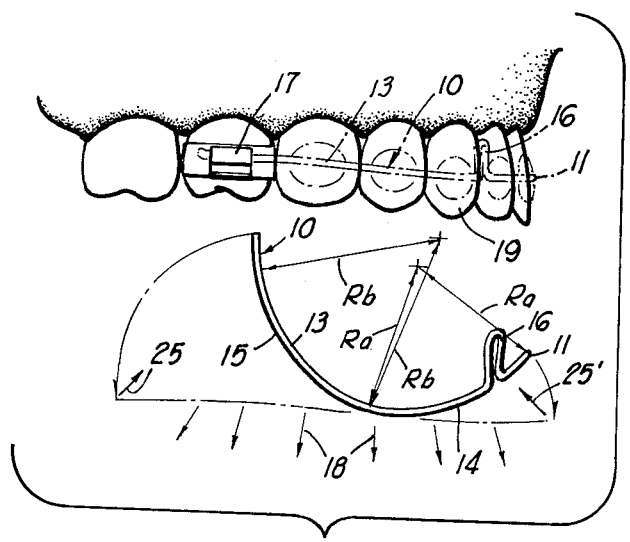
Figure 3:
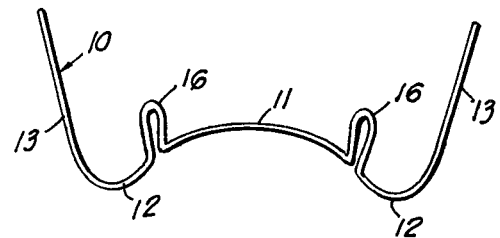
FIG. 3 is a front elevation of the arch wire in FIG. 2.

Referring to FIG. 2, the curvature of the arch wire in a second plane normal to the plane of the natural dental arch is shown. In this second plane, an anterior portion 14 of the arch wire is circularly curved on a first radius Ra and the remaining posterior portion 15 of the device is circularly curved on a radius Rb. Again, the magnitude of these radii will vary from case-to-case but the basic geometry of the compound curve arch wire will be as illustrated in FIGS. 2 and 3A.

Figure 4:
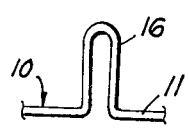
FIG. 4 is a fragmentary elevational view of a tensioned arch wire loop.
Figure 5:
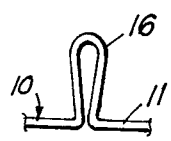
FIG. 5 is a similar view of a relaxed loop.

As required, laterally spaced upstanding space closure loops 16 are pre-formed, as required, in the arch wire 10 during its manufacturing. These loops may be varied in their placement on the wire and in loop length depending upon need as for closing spaces between teeth or maintaining spaces closed. FIGS. 1, 2, 3 and 5 show the loops 16 relaxed as where they would apply no pressure to the teeth, whereas FIG. 4 shows one of the loops spread and under tension for applying closing pressure.

The number of the loops and their spacing on the arch wire may be varied in the invention. When the entire pre-formed compound curve arch wire is resting freely and in a relaxed state, it assumes the shape above-described and shown particularly in FIGS. 2, 3 and 3A.

Figure 1:
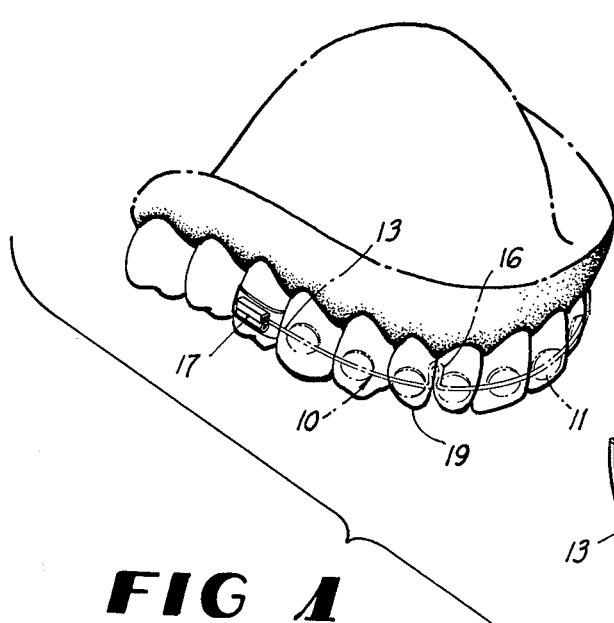
FIG. 1 is an exploded perspective view of the invention.

When the arch wire is applied to the teeth of a patient such as the maxillary, FIGS. 1 and 2, the various portions of the arch wire will be under tension for exerting controlled and consistent pressure on the various teeth including molars, bicuspids, cuspids and incisors, following the necessary adjustment by the orthodontist. For example, brackets 17 are conventionally applied to a pair of the molars and the posterior terminals of the arms 13 are received through tubes of the brackets 17 and secured in the usual manner. This application of the device by the orthodontist straightens the two arms 13 so that the entire arch wire is now substantially disposed in one plane, namely, the plane of the maxillary, FIGS. 1 and 2. The anterior portion 11 of the arch wire is now tending to intrude the incisors and cuspids and the now tensioned arms 13 of the arch wire are exerting consistent and substantially equal forces on the molars and bicuspids, generally as indicated by the force arrows 18 in FIG. 2. The loops 16 are also acting in concert with other parts of the arch wire to exert space closing pressures on adjacent teeth which require this correction, such as the cuspids 19 shown in FIGS. 1 and 2.

It can now be understood that the invention can apply a variable and consistent pressure on all of the teeth in the dental arch simultaneously, in contrast to the application of heavy pressure to certain selected teeth, such as the molars, and little or no pressure to other teeth, such as the incisors. The advantages of the invention should be readily apparent to those skilled in the art.

Figure 6:
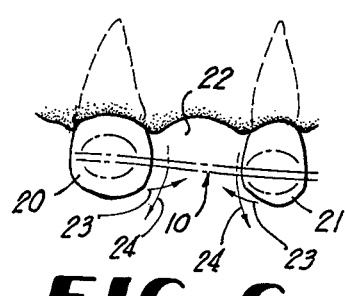
FIG. 6 is a fragmentary partly schematic elevational view illustrating the operation of the invention in relation to teeth at the opposite sides of an extraction space.

FIG. 6 is illustrative of the action of the invention relative to two teeth 20 and 21 on opposite sides of an extraction space 22. The teeth 20 and 21 have a natural tendency to turn in and fill the space 22, as indicated by the arrows 23. This tendency is known as dumping and is not desirable. However, due to the radiating forces 18, these dumping forces are effectively countered as indicated by the force arrows 24 in FIG. 6, all without interfering with cellular activity at the periodontal membrane and also permitting the desired tooth translation in accordance with the main objective of the treatment.

Again referring to FIG. 2, if the anterior teeth require intrusion which is usually the case, then the curved arch wire is very effective since it immediately applies an intrusive force to the central incisors. These forces are shown in FIG. 2 by the vertically inclined force arrows 25 and 25'. The anterior force arrow 25' indicates force toward the posterior and the posterior arrow 25 indicates force toward the anterior. The total operation of the invention, as well as its advantages for the patient and the orthodontist should now be apparent to those skilled in the art.

It is to be understood that the form of the invention herewith shown and described is to be taken as a preferred example of the same, and that various changes in the shape, size and arrangement of parts may be resorted to, without departing from the spirit of the invention or scope of the subjoined claims.

What is claimed is:
1. An orthodontic arch wire for use with orthodontic brackets comprising a unitary spring wire section which is substantially U-shaped in the plane of the natural dental arch and includes laterally spaced arms which are curved throughout the majority of their distal length in a plane substantially perpendicular to the said plane of the said arch, said curves being sloped in one direction only, whereby said arch wire can apply gentle and consistent pressure to all teeth in the dental arch simultaneously.

2. An orthodontic arch wire as defined in claim 1 wherein said arms are curved away from the plane of the natural dental arch toward their distal ends.

3. An orthodontic arch wire as defined in claim 1 wherein said arms include adjacent portions curved on different radii of curvature.

4. An orthodontic arch wire as defined in claim 3 wherein the radii of curvature of the portions of the arms nearest their distal ends are greater than the radii of curvature of the portions adjacent thereto.

5. An orthodontic arch wire as defined in claim 1, and the curvature of the arch wire in each said plane being on substantially circular arcs of curvature.

6. An orthodontic arch wire as defined in claim 5, and said arch wire including substantially straight posteriorly divergent arms in the plane of the natrual dental arch and being continuously curved in said perpendicular plane.

7. An orthodontic arch wire as defined in claim 1, and a pair of spaced spring loops in the arch wire, said loops being normally substantially closed and resisting opening forces due to tensioning of the arch wire.

8. An orthodontic arch wire as defined in claim 7, and said loops being generally U-shaped and rising above the first-named plane of curvature of the arch wire.

9. An orthodontic arch wire as defined in claim 7, wherein the arch wire is shaped during its manufacturing to provide curvature in said perpendicular planes and to form said loops in their relaxed substantially closed conditions.

10. An orthodontic arch wire as defined in claim 1, wherein straightening of said arms in the application of the arch wire to the teeth of an orthodontic patient tensions said arms and enables the arch wire to apply pressure to substantially all of the teeth in the dental arch.

11. An orthodontic arch wire as defined in claim 1, and a pair of spaced spring loops in the arch wire, said loops being normally substantially closed and resisting opening forces due to tensioning of the arch wire.

12. An orthodontic arch wire as defined in claim 11, and said loops being generally U-shaped and rising above the first-named plane of curvature of the arch wire.

13. An orthodontic arch wire as defined in claim 11, wherein the arch wire is shaped during its manufacturing to provide curvature in said perpendicular planes and to form said loops in their relaxed substantially closed conditions.

* * * * *